United States Patent [19]

Sancoff et al.

[11] Patent Number: 5,766,147
[45] Date of Patent: *Jun. 16, 1998

[54] VIAL ADAPTOR FOR A LIQUID DELIVERY DEVICE

[75] Inventors: Gregory E. Sancoff, Windham, N.H.; Mark C. Doyle, San Diego; Frederic P. Field, Solana Beach, both of Calif.

[73] Assignee: Winfield Medical, San Diego, Calif.

[*] Notice: The term of this patent shall not extend beyond the expiration date of Pat. No. 5,397,303.

[21] Appl. No.: 488,037

[22] Filed: Jun. 7, 1995

[51] Int. Cl.⁶ .................................................. A61M 31/00
[52] U.S. Cl. .............................. 604/56; 604/92; 604/416; 141/2
[58] Field of Search ............................ 604/82–92, 140, 604/131, 132, 142, 145–148, 416, 56; 141/2

[56] References Cited

U.S. PATENT DOCUMENTS

| | | |
|---|---|---|
| 3,718,236 | 2/1973 | Reyner et al. |
| 3,840,009 | 10/1974 | Michaels et al. |
| 3,894,538 | 7/1975 | Ricther |
| 4,019,512 | 4/1977 | Tenczar |
| 4,049,158 | 9/1977 | Lo et al. |
| 4,128,098 | 12/1978 | Bloom et al. |
| 4,203,441 | 5/1980 | Theeuwes |
| 4,253,501 | 3/1981 | Ogle |
| 4,337,769 | 7/1982 | Olson |
| 4,360,131 | 11/1982 | Reyner |
| 4,373,341 | 2/1983 | Mahaffy et al. |
| 4,376,500 | 3/1983 | Banks et al. |
| 4,379,453 | 4/1983 | Baron |
| 4,410,321 | 10/1983 | Pearson, et al. |
| 4,411,662 | 10/1983 | Pearson |
| 4,432,755 | 2/1984 | Pearson |
| 4,458,733 | 7/1984 | Lyons |
| 4,478,044 | 10/1984 | Magid |
| 4,491,250 | 1/1985 | Liebermann |
| 4,507,116 | 3/1985 | Leibinsohn |
| 4,510,734 | 4/1985 | Banks et al. |
| 4,513,884 | 4/1985 | Magid |
| 4,515,586 | 5/1985 | Mendenhall et al. |
| 4,518,103 | 5/1985 | Lim et al. |
| 4,553,685 | 11/1985 | Magid |
| 4,583,971 | 4/1986 | Bocquet et al. |
| 4,606,734 | 8/1986 | Larkin et al. |
| 4,614,515 | 9/1986 | Tripp et al. |
| 4,640,445 | 2/1987 | Yamada |
| 4,646,946 | 3/1987 | Reyner |
| 4,648,955 | 3/1987 | Maget |
| 4,675,020 | 6/1987 | McPhee |
| 4,679,706 | 7/1987 | Magid et al. |
| 4,687,423 | 8/1987 | Maget et al. |
| 4,759,756 | 7/1988 | Forman et al. |
| 4,768,568 | 9/1988 | Fournier et al. |
| 4,781,679 | 11/1988 | Larkin |
| 4,804,366 | 2/1989 | Zdeb et al. |
| 4,834,152 | 5/1989 | Howson et al. |
| 4,850,978 | 7/1989 | Dudar et al. |
| 4,863,454 | 9/1989 | La Bove |
| 4,886,514 | 12/1989 | Maget |
| 4,898,209 | 2/1990 | Zdeb |
| 4,923,095 | 5/1990 | Dorfman et al. |
| 4,936,829 | 6/1990 | Zdeb et al. |
| 4,936,841 | 6/1990 | Aoki et al. |
| 5,022,564 | 6/1991 | Reyner |

(List continued on next page.)

FOREIGN PATENT DOCUMENTS

WO 95/05211  2/1995  WIPO.

*Primary Examiner*—Mark Bockelman
*Attorney, Agent, or Firm*—Knobbe, Martens, Olson & Bear, LLP

[57] ABSTRACT

A device is disclosed which provides for direct incorporation of a substance from a separate container, such as a drug vial, into the contents of a liquid delivery device, which has a connecter to provide communication between the device and the container, and means for closing the connection prior to dispensing the contents of the device. A method for permitting a substance in a container to be transferred to a liquid delivery device, and contents of the device to be administered to a patient is also disclosed.

13 Claims, 9 Drawing Sheets

U.S. PATENT DOCUMENTS

| | | |
|---|---|---|
| 5,024,657 | 6/1991 | Needlham et al. . |
| 5,049,129 | 9/1991 | Zdeb et al. . |
| 5,054,651 | 10/1991 | Morane . |
| 5,064,059 | 11/1991 | Ziegler et al. . |
| 5,080,652 | 1/1992 | Sancoff et al. . |
| 5,106,374 | 4/1992 | Apperson et al. . |
| 5,116,316 | 5/1992 | Sertic et al. . |
| 5,137,186 | 8/1992 | Moran . |
| 5,167,631 | 12/1992 | Thompson et al. . |
| 5,167,816 | 12/1992 | Kruger et al. . |
| 5,171,214 | 12/1992 | Kolber et al. . |
| 5,232,029 | 8/1993 | Knox et al. . |
| 5,304,163 | 4/1994 | Bonnici et al. . |
| 5,391,150 | 2/1995 | Richmond . |
| 5,397,303 | 3/1995 | Sancoff et al. . |
| 5,398,851 | 3/1995 | Sancoff et al. . |

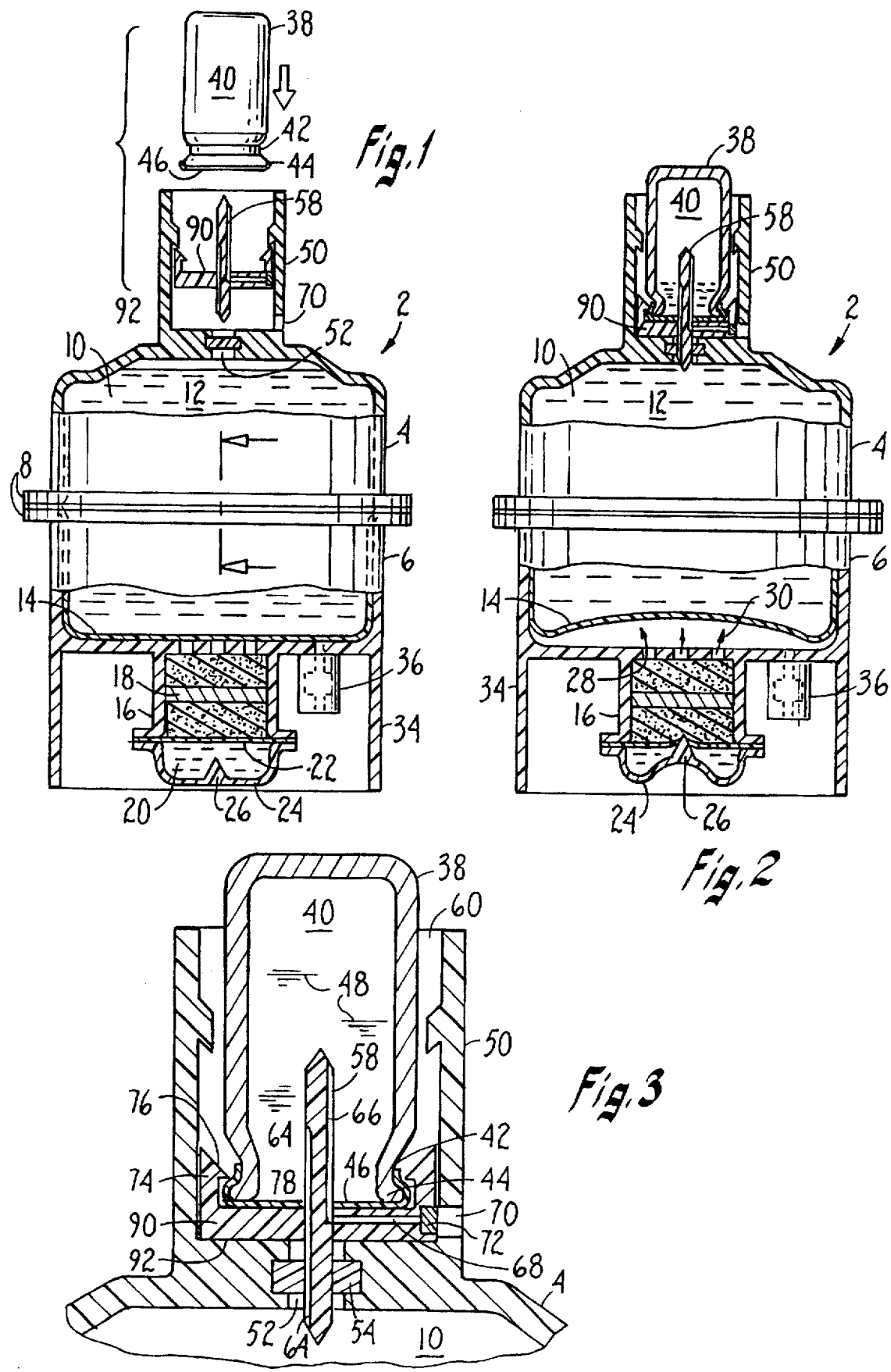

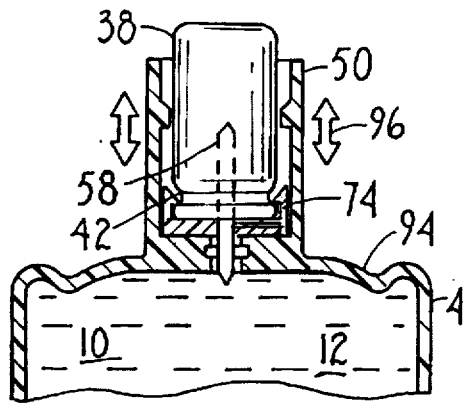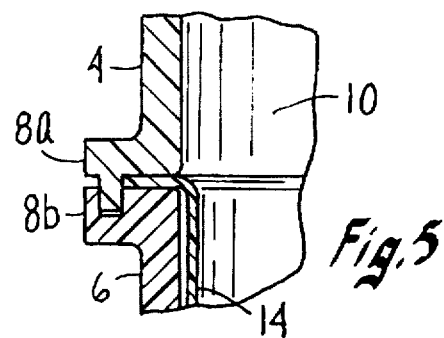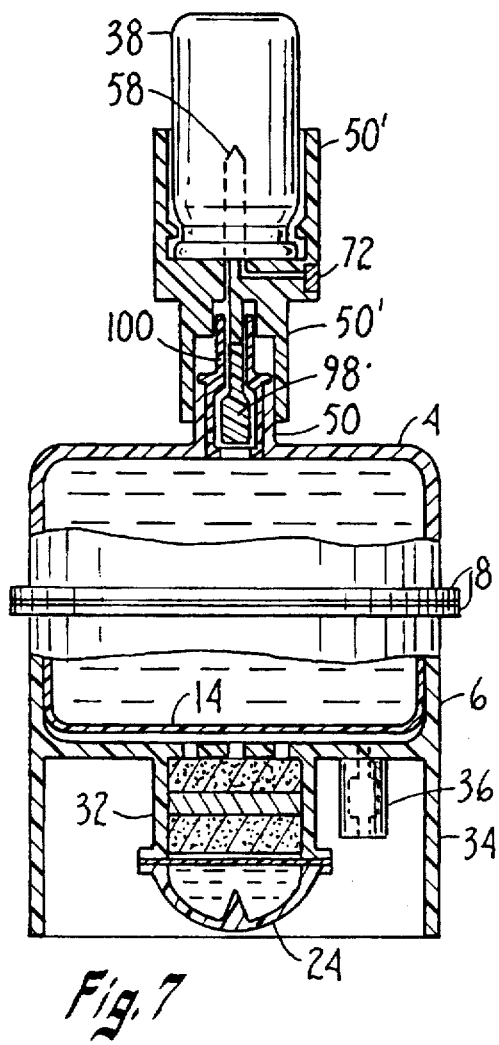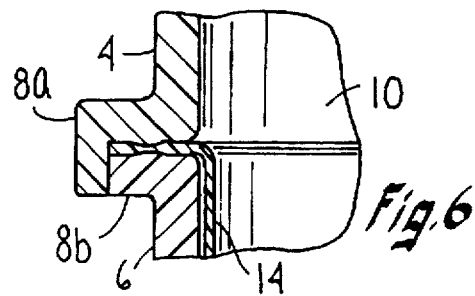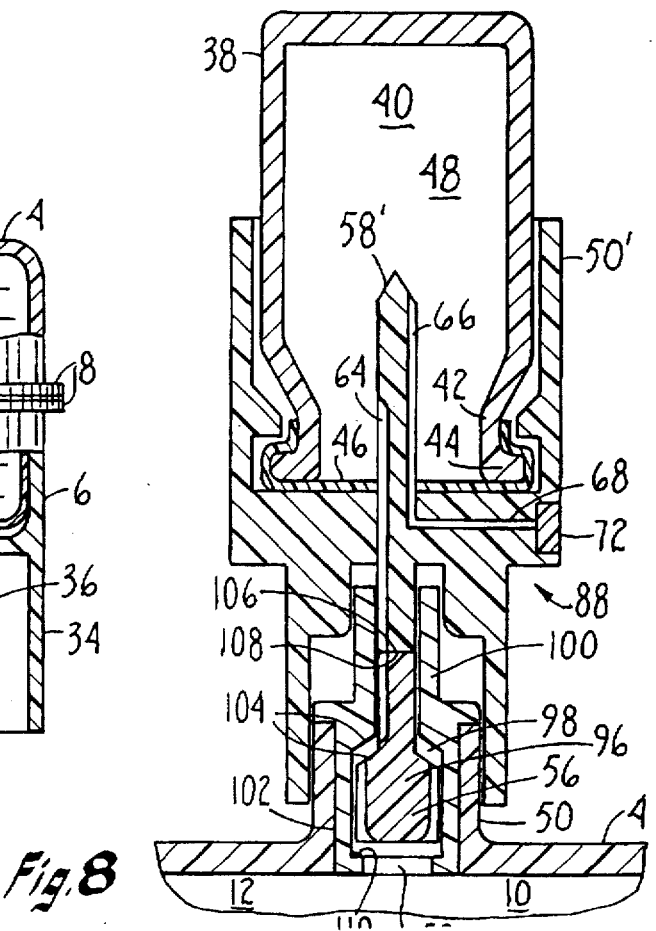

5,766,147

VIAL ADAPTOR FOR A LIQUID DELIVERY DEVICE

BACKGROUND OF THE INVENTION

1. Field of the Invention

The present invention relates to liquid delivery devices such as medicine dispensers More particularly it relates to liquid delivery devices having an adapter that permits a substance in a vial or other separate container to be transferred to such delivery device before the contents of the device are dispersed.

2. Description of the Prior Art

There are a number of types of liquid delivery devices or dispensers that are intended to provide for the delivery of a liquid medication to a patient under controlled conditions. One well known device of this type is the common I.V. bag which uses gravity to dispense the fluid contained therein. Other devices are shown in U.S. Pat. Nos. 5,080,652 and 5,398,851 to G. E. Sancoff, et al. These delivery devices utilize different mechanisms to cause a liquid contained therein (often a solution containing one or more medications) to be dispensed either continually or intermittently from the container, normally through a conduit which terminates at its distal end with an attachment for intravenous, subcutaneous, or intraparenteral administration to a patient.

Such devices may be stored in an empty condition and then filled with the liquid medication shortly before or at the time of administration of the medication to the patient. Alternatively, containers can be stored in a sealed condition but filled with a liquid medication or liquid medium; at the time of administration the device is opened and the medication dispensed to the patient as indicated above. In many instances it is desirable to incorporate additional or different medications into the liquid medication already present in the device. In other instances where the device is filled with a neutral liquid medium, it is necessary to add the medication to that medium prior to dispensing the contents to the patient. The latter commonly occurs when the particular medication to be delivered has a short shelf life or where it is effective only for a short period after being dispersed in the liquid medium.

In both of these cases, it is necessary to establish some sort of fluid connection between the device and the container holding the additional or separate medicine. With many devices this is either difficult or impossible to do, and thus requires a second administration of the additional or other medicine to the patient.

A primary failing of the prior art vial adapters has been the failure to provide a resealable attachment. Therefore, when a vial is disposed on the diluent source it cannot be removed without the loss of diluent or medication. Moreover, removal of the vial is preferable so as to minimize the volume of diluent and medicament lost in line.

Accordingly, a need exists for an infusion device with a vial adapter associated therewith that allows for the efficient and expeditious transfer of a medication into the infusion device and that further allows the vial or other container initially containing the medication to be removed, or the connection between the two to be reversibly sealed, and the device put on line to the patient.

SUMMARY OF THE INVENTION

The present invention provides several embodiments of resealable adapters that can be used for the introduction of a medicament from a drug vial, for example, into an infusion device or IV bag followed by the delivery of the medicament to a patient. A profound feature of the present invention is that, in a preferred embodiment, it provides an openable and closeable channel through which the medicament can be delivered to the infusion device, thereafter allowing the vial to be removed and/or the device to be pressurized to deliver the fluid.

This aspect of the present invention stands in stark contrast to the prior art. In the prior art, many complicated structures were used to achieve the objective of the present invention.

A first aspect of the present invention provides a method for permitting a substance in a vial to be transferred to a liquid delivery device, and contents of the delivery device to be administered to a patient. The method comprises the steps of connecting the vial to the delivery device, introducing the substance from the vial into the delivery device, closing the connection between the vial and the delivery device, and pressurizing the contents of the delivery device for administration to the patient. The vial can be removed from the delivery device after the connection between the vial and the device is closed.

The introducing step preferably comprises introducing a liquid contained in the delivery device into the vial, and thereafter introducing the liquid in the vial back into the delivery device.

The closing step is preferably reversible, and can be achieved by means of a valve, or a clamp. The delivery device can be an I.V. bag or a pressure infusion device.

Another aspect of the present invention provides a method for permitting a solid substance in a vial to be transferred to a liquid delivery device containing a diluent, and contents of the device to be thereafter administered to a patient. This method comprises the steps of connecting the vial to the device, introducing a portion of the diluent into the vial through the connection to dissolve the solid substance, returning the portion of the diluent and the dissolved solid substance into the device, closing the connection between the vial and the device, and administering the contents of the device to the patient. The contents of the device can be pressurized prior to administration to the patient. If desired, the introducing and returning steps can be repeated until the solid is substantially dissolved in the diluent. Preferably, the vial is removed from the device after the connection between the vial and the device is closed, however, the vial can also be left in place with the connection closed.

The closing step is preferably reversible, and can be accomplished by means of a valve or a clamp. The delivery device can be an I.V. bag or a pressure infusion device.

BRIEF DESCRIPTION OF THE DRAWINGS

FIG. 1 is a side elevation view, with portions cut away, of one configuration of the liquid delivery device of the present invention.

FIG. 2 is a similar view with pressurized infusion in operation.

FIG. 3 is an enlarged view of the upper portion of FIG. 2.

FIG. 4 is a view similar to a portion of FIG. 2 showing manual compression of the delivery device.

FIG. 5 is an enlarged sectional view taken on line 5—5 of FIG. 1.

FIG. 6 is a sectional view similar to that of FIG. 5 showing an alternative rim configuration.

FIG. 7 is a side elevation view, with portions cut away, of an alternative device with a separate adapter to hold the vial.

FIG. 8 is an enlarged view of the upper portion of FIG. 7.

DETAILED DESCRIPTION OF THE PREFERRED EMBODIMENTS

Figure 9:
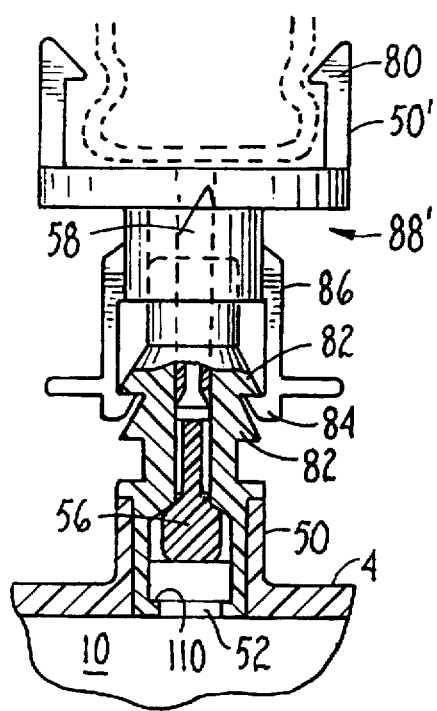
FIG. 9 is a partially cut away view of an alternative adapter arrangement in storage position.

The present invention is related to an attachment or an adapter that allows for the addition of a medication from a container holding the medication to a solution contained within a liquid delivery or dispensing device. It will be understood that often drugs or medications, following their manufacture, are packaged within containers that allow the medication to be kept sterile. Glass vials are frequently used; glass is highly inert, very stable, is readily sterilizable, and can be used with virtually any medication, whether it is a solid or liquid. The vials usually have a rubber septum at their mouths that allow for the reconstitution, dilution, and/or simple transfer of the medication from the vial through use of a needle and syringe.

The present invention allows for similar ease of transfer without the need for the use of a needle and syringe. Rather, the invention allows a vial to be essentially attached to a liquid delivery device and the medication contained in the vial transferred to the device easily and without contamination. The connection between the vial and the device can then be closed, allowing the infusion device to be pressurized if necessary to deliver the liquid contained therein without pressurizing the drug vial, which might result in loss of solution, leakage, or vial explosion. The connection between the vial and the liquid delivery device can be reopened at any time. This is accomplished in the broadest sense by having a first connector sized to fit around the mouth of a drug vial that has a piercing means to perforate the septum in the vial, a channel extending from the connector that will allow the communication of the medication from the vial to the delivery device, and a second connector that is attached to the device. Preferably, the channel additionally contains means for reversibly preventing communication of the medication from the drug vial to the device and/or communication of the diluent from the device to the drug vial.

As discussed above, the medication contained in the drug vial can be a liquid or a solid and the principle of the invention is to move the medication from the vial to the liquid delivery device. When the medication is a liquid, it will be understood that it will easily flow through the channel into the delivery device. Dilution of the liquid contents of the vial may still be desired, however, to enable the complete transfer of the contents of the vial. When the medication is a solid, it is necessary to reconstitute the solid. This may be accomplished either through adding a solvent to the solid while it is in the vial or a solvent in the device can be communicated through the channel to the vial and the reconstituted medication can be communicated back to the device.

The latter process is preferred, since, many medications are less stable in solution and begin to lose their efficacy the longer they are maintained in solution. This is a primary reason that such medications have been packaged and sold as solids in the first place. Therefore, it will be understood that it is highly advantageous to be able to reconstitute solid medications, just prior to administration to the patient.

It is also desirable to close the channel between the device and the drug vial to allow the contents of the device to be pressurized to facilitate delivery of the contents from the device. Should the channel remain open, liquid from the device can be forced back into the vial, resulting in loss of medication, leakage, and explosion of the drug vial. Also, it is often desirable to remove the drug vial from the device after transfer of the vial contents to the device is complete. Accordingly, the present invention provides an openable and closeable channel between the drug vial and the device.

The vial adaptor structure that meets the abovediscussed requirements of the present invention will be best understood by reference to the drawings. FIGS. 1, 2, 4 and 11 show overall views of different embodiments of the present device with the connecting structure incorporated therein and showing the connection with the separate container, here illustrated as a vial. In FIGS. 1 and 2, the device shown is that described and claimed in U.S Pat. No. 5,397,303, the disclosure of which is hereby incorporated by reference. The details of the operation of that device, including the means for dispensing the contained liquid, may be understood by reference thereto. However, the vial adaptor and connecting structure of the present invention is adapted for use with any device which is used to deliver fluid including a conventional I.V. bag. The device described below is for the purpose of illustration only.

A liquid delivery device 2 of this type is commonly formed of two parts 4 and 6 which are joined in a convenient manner, as by mating flanges 8. The device 2 is hollow with an interior 10 shown as filled with a liquid 12. The liquid 12 may be a medication itself, or it may be an inert carrier liquid into which a medication is subsequently incorporated, as will be described below.

It will be understood that the descriptions herein as to "medication" is merely for the purpose of example, and that a variety of other types of fluids and added materials, such as intravenous nutrients, may be mixed and dispensed with the device of this invention. Those skilled in the art will be well aware of the many materials which can be handled by this device, and can readily determine the optimum manner of handling any particular combination of materials.

Dispensing of the liquid is by means of motion of membrane 14 by the pressure of gas which is evolved by the reaction of two chemicals which are initially separated but are brought together and allowed to react and evolve the gas. The chemicals are conveniently housed in a well 16 attached to the wall of portion 6 of container 2. One of the chemicals is illustrated in the form of a solid pellet 18 and the other is in the form of liquid 20. The two are separated by membrane 22. When a flexible cap 24 surrounding liquid 20 is flexed, as shown in FIG. 2, a sharp protuberance 26 on the inside of dome 24 perforates membrane 22, allowing liquid chemical 20 to flow into contact with chemical 18, evolving gas which escapes through openings 28 as indicated by arrows 30, thus pushing membrane 14 forward as indicated in FIG. 2 and causing the liquid to be dispensed through outlet 32 (visible in FIG. 11). Membrane 14 is secured at its periphery by being clamped between the flanges 8 (designated as 8a and 8b in FIGS. 5 and 6).

If desired, the device 2 can have a skirt 34 surrounding the well 16 to allow the device to be placed on end and to protect the well 16 and dome 24 against accidental activation of the chemicals. Also present may be gas relief valve 36 which serves to control any overpressure from the evolving gas and also to allow the device 2 to be maintained at a predetermined pressure during administration of the medication.

For the purposes of illustration herein, the liquid 12 will hereafter be referred to simply as the carrier liquid, and it will be assumed that there is no medication initially present in the liquid 12. It will of course be understood that this is solely for the purpose of illustration and that as noted above in fact there are many instances in which the liquid 12 may itself be a medication. The medicating substance 48 is initially contained in separate container 38, here illustrated as a vial. The medication 48 will be present within interior 40 of vial 38 and may be either in liquid form or in the form of a readily soluble solid material, usually a powder or granulated material. The vial 38 normally has a reduced collar area 42 widening to a lip 44, and is sealed by a membrane or cap 46. The purpose of the structure of the invention herein is to permit the medication 48 to be transferred from the vial 38 to the interior of the device 2 to be incorporated into the carrier fluid 12. The connection between the interiors of the vial 38 and the device 2 can then be closed to allow the fluid to be pressured for delivery to the patient.

Figure 10:
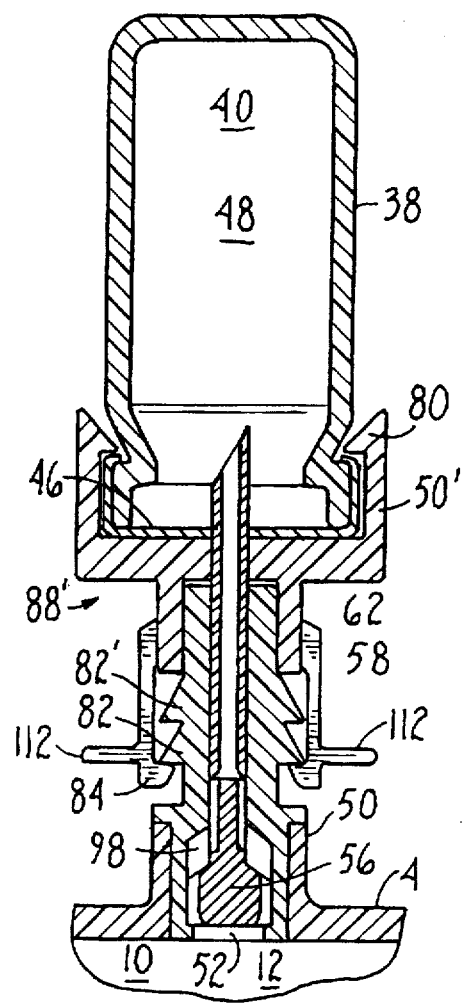
FIG. 10 is a similar view with the vial in the adapter.
Figure 11:
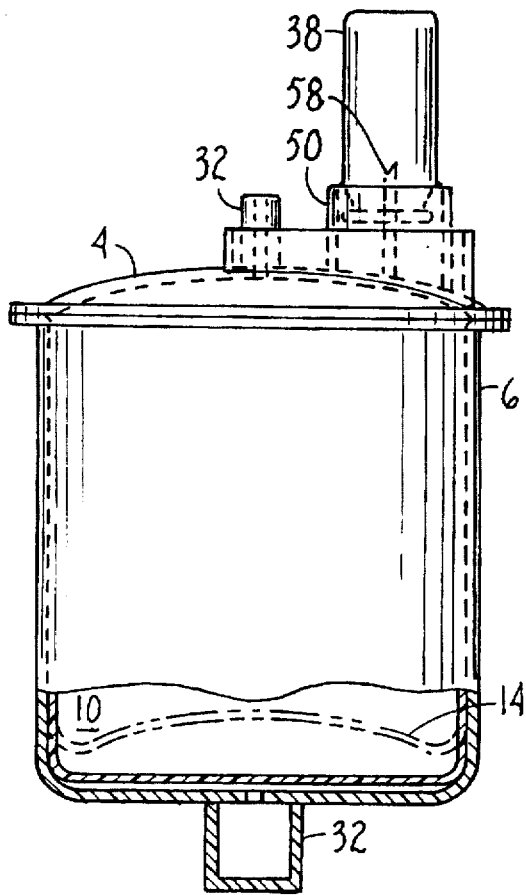
FIG. 11 is a side elevation view of a further configuration of the apparatus.

The concept is best understood by reference to FIG. 3. At the top of portion 4 is formed a sleeve-like member or connector 50 which surrounds an opening 52 leading from the interior 10 of device 2 to the exterior of the device 2 in the open hollow middle of the sleeve 50. The inside diameter of the sleeve 50 is sufficiently large to be able to accommodate either the entire diameter of vial 38 as shown or at least the upper neck portion including neck 42 and rim 44 (as illustrated in FIGS. 10 and 11). The opening 52 of the device is closed by any convenient means, such as a plug, an elastomeric septum, or a valve; alternatively, or in addition, the sleeve or connector can be sealed at either end by means of a plug, valve, elastomeric septum or clamp, as will be described in more detail below. Also present will be a fluid communication member, normally in the form of a needle 58, the structure of which will also be described below.

In one form of usage herein the vial 38 is positioned above the opening 60 of sleeve 50 and is pushed downward to make contact with needle 58. Needle 58 penetrates through the cap 46 of vial 38 and also penetrates through the closure 54 so that the opposite ends of needle 58 are positioned respectively in the medication 48 within interior 40 and in the carrier liquid 12 in interior 10. Fluid communication may be either by a hollow axial conduit 62 through needle 58, as shown in FIG. 10, or through a conduit formed by a groove 64 formed in one side of the needle 58. There is also alternatively a second groove or conduit 66 (shown in FIG. 3) which passes through only a portion of the needle 58 and terminates in a junction with a conduit 68 which in turn extends to an opening 70 in sleeve which provides access to the ambient atmosphere. Thus as the medication 48 is withdrawn from the vial 38, air or other ambient gas can pass into the interior 40 through conduits 66 and 68 and hole 70 so that the formation of a vacuum and subsequently restricted flow of medication 48 is prevented. Typically there will also be a filter 72 present to remove any unwanted material from the ambient air as it passes from hole 70 into conduit 68.

It will be understood that other types of vial openers can be used in the present invention in place of the needle 58. Such openers can include, for example, vial cap removers, cutters, ampoule openers, and the like.

Within sleeve 50, there is preferably a vial securing device 74 which contains means (illustrated in FIG. 3 as flange 76) to engage a corresponding depression or groove 78 in the neck 42 of vial 38. The flange 76, and usually the entire member 74, will have some degree of resiliency so that the vial 38 can be pushed forward so that rim 44 passes the flange or shoulder 76 and allows the grooved area 78 to cooperate with the flange 76 to prevent unwanted disengagement of the vial 38 from securement within the sleeve 50. Other means of securement can be in the form of tabs 80 formed on the outer end of sleeve 50 as shown in FIG. 10 or as radial structures in the forms of truncated cones 82 and 82' which are engaged by the hooks 84 of an external sleeve 86.

In some embodiments the sleeve will be in the form of a sleeve assembly which is formed of a sleeve 50 attached to the wall of portion 4 and a male/female coupling member 88 which has a secondary sleeve 50' into which the vial 38 fits (FIG. 8). This use of the coupling device 88 permits the entire assembly to be removed from the device 2 so that the sleeve 50 and opening 52 can if desired be subsequently used as an outlet equivalent to outlet 32 once the contents of vial 38 have been incorporated into the fluid 12. In the embodiment shown in FIG. 1, the needle 58 is initially retained in a sliding plate 90 which is depressed downward by the positioning of vial 38, eventually coming to rest against the bottom 92 of sleeve 50 once the needle 58 has penetrated through the plug 54. The continued movement of vial 38 then causes the needle 58 to penetrate the cap 46 to establish a fluid communication between the vial 38 and the dispensing device 2.

Once the vial is in place and secured, as shown in FIG. 3, the transfer of the contents 48 of vial 38 is commenced. The contents 48 may initially be under some pressure and therefore be forced through needle 58 into liquid carrier 12. Alternatively, however, it is preferred to have the top portion 4 of the device 2 be somewhat flexible, as illustrated in FIG. 4 at 94. When the portion 94 is flexed as indicated by arrows 96, the formation of a reduced pressure in interior 10 causes the contents 48 of vial 38 to be rapidly drawn out of the interior 40 and into fluid 12. Mixing is preferably accomplished by moving or pumping the fluid back and forth between the interior 40 and the fluid 12.

It is desirable to have means for closing the channel between the drug vial and the delivery device after the contents of the vial have been transferred to the device. In one embodiment, a one-way valve 56 is present in the sleeve 50, which valve 56 is activated by contact with needle 58 when the vial 38 is pressed into place. This may be best seen in FIGS. 8 and 9. In this case, valve 56 is in the form of a bottle shaped plug 96, which conforms to a funnel-shaped interior 98 in a plug 100 which is fitted into sleeve 50 with an interference fit so that it is retained by friction on the mating surfaces 102. The plug 98 can be buoyant so that any fluid in container 12 forces it up into the opening 98 and closes the valve by contact between the surfaces 104. Or, in a preferred embodiment, the plug is restrained under mechanical pressure or is a compression fitting, which is opened by compression or force in a direction opposite the compression. When the needle 58 or needle-like structure 58' is pushed downward by the force of position of vial 38, the bottom 106 of the needle 58 or needle-like structure 58' contacts the top 108 of the plug 96 and forces it downward, thus opening the gap 98 to allow the liquid 12 to flow upward into the vial or the material 48 to flow toward the device 2 either because the material 48 is a liquid initially or because it becomes dissolved in that portion of the liquid 12 which passes into the interior 40 of vial 38. The plug 96 is prevented from falling out of the position by shoulders 110 of plug 100.

Figure 22:
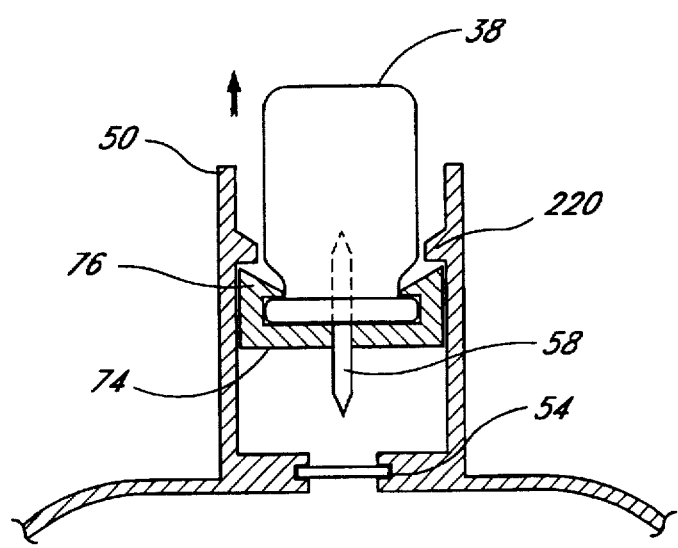
FIG. 22 is an enlarged view of an alternate embodiment of the upper portion of the liquid delivery device, showing the vial adaptor in a retracted position.

In an alternate embodiment of the vial adaptor, illustrated in FIG. 22, the vial 38 and vial securing device 74, which are connected, can be retracted after transfer of the medication to seal the device. The opening to the delivery device is preferably sealed with an elastomeric septum or closure 54, which is pierced by the needle 58 to allow communication between the interior of the vial 38 and the interior of the device. To prevent the communication between the vial 38 and the device, the vial 38 is moved in the direction of the arrow, away from the device. Flange 76 on the vial securing device 74 contacts the corresponding flange 220 on the inside of the sleeve 50. In this retracted position, the needle 58 is withdrawn from the elastomeric closure 54 which reseals due to its inherently elastic nature.

Figure 18:
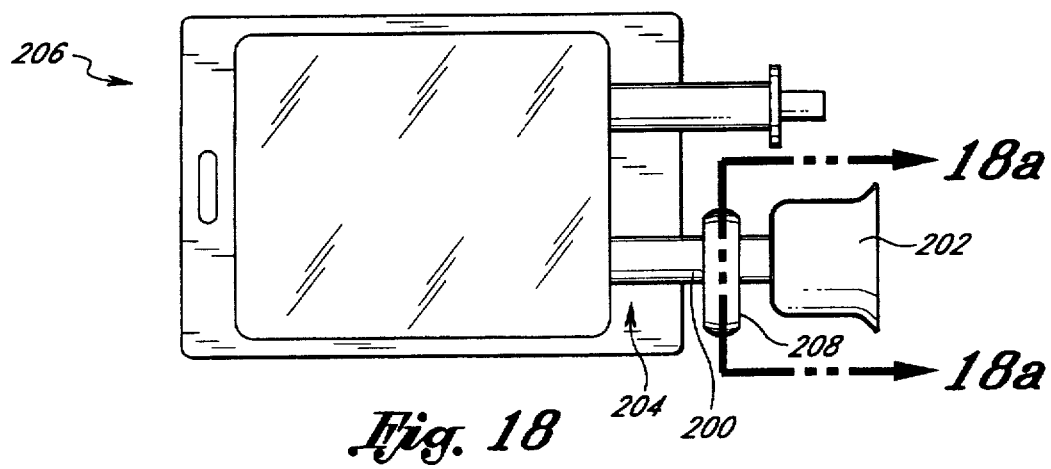
FIG. 18 is a top view of a liquid delivery device having a vial adaptor in accordance with the present invention and a clamp which closes the connection between the interior of the dispensing device and the interior of the vial.
Figure 18A:
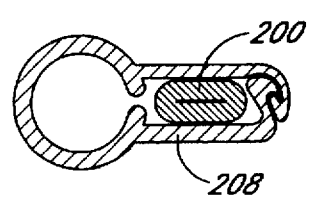
FIG. 18a is a cross-sectional view taken along line 18a of FIG. 18, with the clamp in a closed position.
Figure 18B:
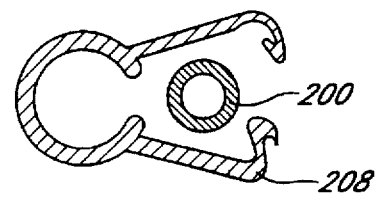
FIG. 18b is a similar view to FIG. 18a, with the clamp in an open position.

Alternatively, the means for closing the channel between the drug vial and the liquid delivery device can comprise a clamp. As illustrated in FIG. 18, a channel 200 joins the vial adaptor 202 to a port 204 located in the liquid delivery device, here illustrated as an I.V. bag 206. This channel 200 is surrounded by a clamp 208. A drug vial (not shown) is attached to the vial adaptor 202 which, as described above, accommodates the upper portion of the vial and includes a needle which penetrates the cap of the vial to provide communication between the interior of the vial and the interior of the device 206. The clamp 208 is opened to allow exchange between the interior of the vial and the interior of the device 206, as shown in FIG. 18b. After the contents of the vial are transferred to the device 206, the clamp 208 is closed, sealing the connection between the vial and the device 206 as shown in FIG. 18a. This allows the liquid in the device 206 to be pressurized for delivery to the patient, and prevents the undesired flow of liquid from the device 206 into the vial. If desired, the vial can be removed from the vial adaptor after the contents have been transferred to the device 206.

Figure 19:
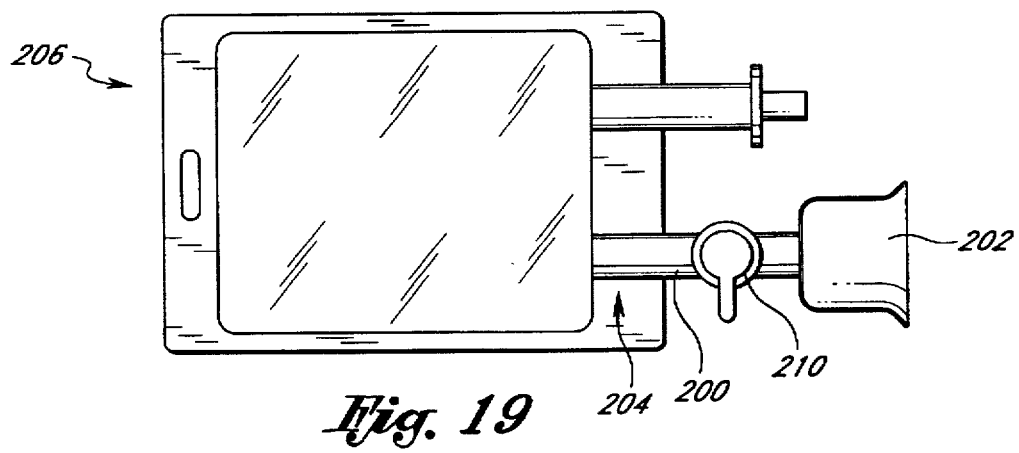
FIG. 19 is similar to FIG. 18, however, the clamp has been replaced with a valve.
Figure 19A:
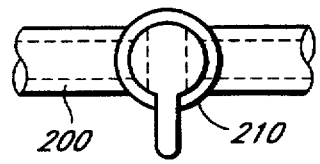
FIG. 19a is a top view of the valve of FIG. 19 in a closed position.
Figure 19B:
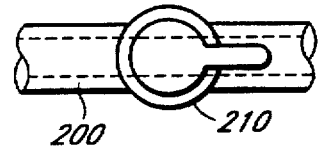
FIG. 19b is a top view of the valve of FIG. 19 in an open position.

In FIG. 19, there is illustrated a valve 210 positioned in the channel 200 joining the vial adaptor 202 to the liquid delivery device 206. Unlike the valve described above, this valve 210 is manually openable and closeable from the exterior of the device 206. When the valve 210 is open, the exchange of contents between the interiors of the vial and the device 206 is achieved, as shown in FIG. 19b. The valve 210 is closed to prevent further fluid exchange between the device 206 and the vial during pressurization of the contents of the device 206 to facilitate administration to the patient, as shown in FIG. 19a. The closing of the valve 210 allows for the removal of the vial from the vial adaptor 202, if desired, even when the contents of the device 206 are pressurized.

Figure 20:
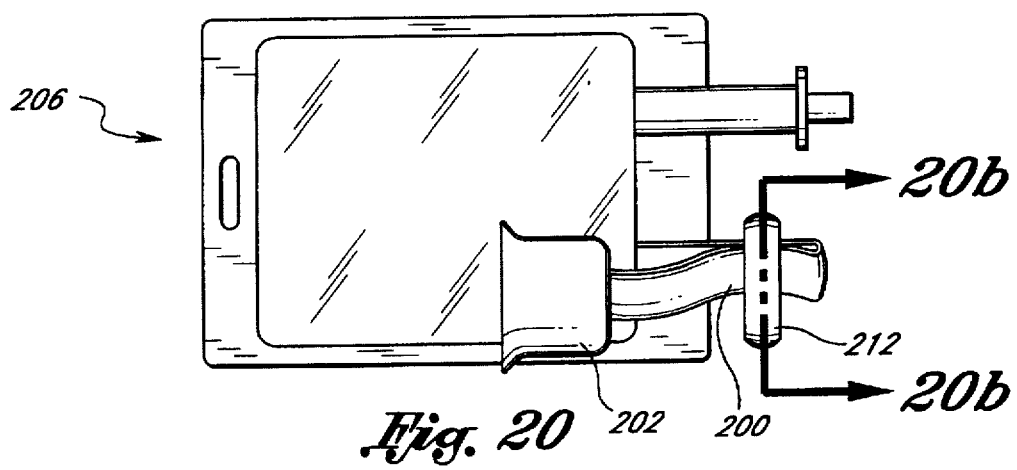
FIG. 20 is a top view of an alternate embodiment of a liquid delivery device having a vial adaptor in accordance with the present invention and a clamp which closes the connection between the interior of the dispensing device and the interior of the vial.
Figure 20A:
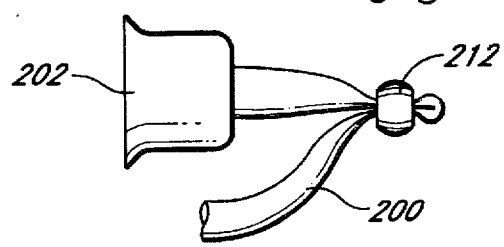
FIG. 20a is a side view of the clamp of FIG. 20 closing the connection between the interior of the delivery device and the interior of the vial.
Figure 20B:
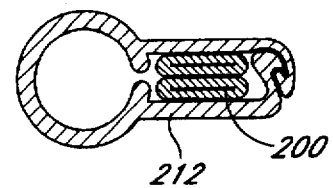
FIG. 20b is a cross-sectional view taken along line 20b in FIG. 20, with the clamp in a closed position.
Figure 21:
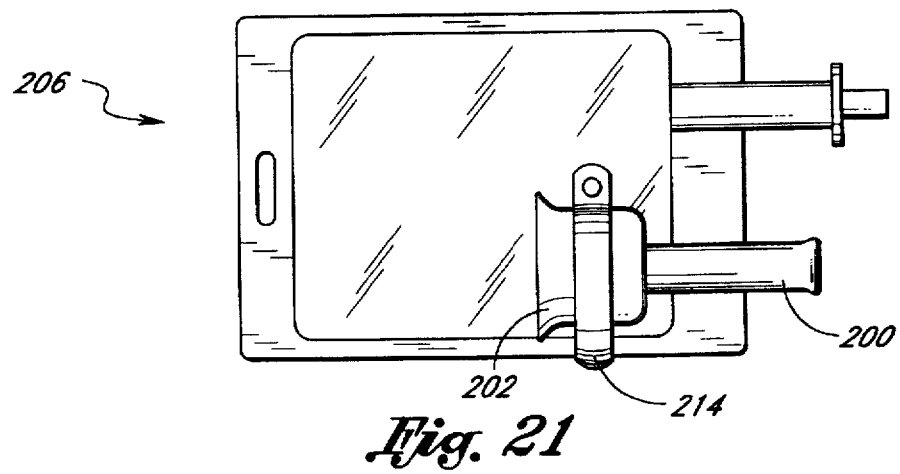
FIG. 21 is a top view of an alternate embodiment of a liquid delivery device having a vial adaptor in accordance with the present invention.
Figure 21A:
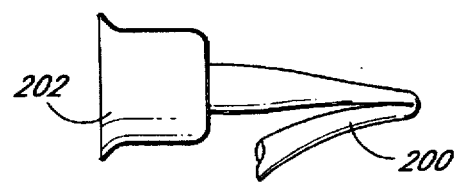
FIG. 21a is a side view of the vial adaptor and tubing of FIG. 21.

Additional means for closing the channel 200 between the drug vial and the liquid delivery device 206 are illustrated in FIGS. 20 and 21. FIG. 20 illustrates means by which the channel 200 is folded and clamped by means of a clamp 212 surrounding the channel 200, thereby reversibly sealing the connection between the interiors of the vial and the device 206, as shown in more detail in FIGS. 20a and 20b. Alternatively, as illustrated in FIG. 21, the channel 200 is folded over and the vial adaptor 202 is reversibly attached to the device 206, which closes the channel 200 connecting the adaptor 202 to the device 206, as illustrated in FIG. 21a. The attachment of the vial adaptor 202 to the device 206 can be achieved by means 214 such as tape, a strap, a clip or the like.

Other means for reversibly closing the channel between the drug vial and the liquid delivery device will suggest themselves to those of ordinary skill in the art. The means described herein are for purposes of illustration, and not limitation.

When it is desired to administer a liquid to a patient, the drug vial is attached to the vial adaptor 202, the needle or other vial opening device within the vial adaptor 202 opens the top of the vial, and the channel 200 between the vial and the liquid delivery device 206 is opened, for example, by opening the clamp 208. The liquid inside the vial is transferred to the interior of the device 206 through the needle and the channel 200. If the vial contains a solid, liquid from the interior of the device 206 can be first communicated through the channel 200 and the needle in the vial adaptor 202 and into the vial to dissolve the solid. The liquid containing the dissolved solid is then transferred back into the device 206. This procedure can be repeated until substantially all of the solid has been dissolved and transferred to the device 206. The liquid contained in the device 206 is then administered to the patient. If desired, the connection between the vial and the device 206 can be re-closed before administration of the liquid inside the device 206, allowing the liquid to be pressurized for ease of administration. Preferably, the vial is removed from the adaptor 202 before pressurization and administration of the liquid begins. After the vial is removed, the liquid can be dispensed through a separate port in the dispensing device 206, or through the connector 200 as described above, eliminating the need for multiple ports in the device 206.

Turning again to FIG. 9, it is often desirable to be able to have the vial 38 and delivery device 2 loosely attached together as for shipping and storing, but positioned apart so that the needle 58 or needle-like structure 58' is not penetrating into fluid communication with either of the vessels. The two vessels are positioned so that a simple push on the vial 38 will cause the two to come into operative position and the medication 48 and the carrier material 12 to be properly mixed. This permits, for instance, medications and carrier materials to be shipped and stored together and to be immediately available as in an emergency situation. For instance, storage of medications in a hospital emergency room must be such that the emergency room personnel can immediately obtain the exact medications needed and do not need to look for two or more separate containers which may be stored at different locations or of which one may have simply not been properly replenished. In order to avoid premature activation of the medication system and to preserve the shelf life of the medication for the maximum period, it is necessary however to have the vessels connected but remain sufficiently far apart that neither one becomes inadvertently opened and the contents then exposed and subject to subsequent deterioration.

A structure to accomplish this is shown in FIG. 9 in which there are two separate securing conical flanges 82 and 82' which are spaced some distance apart. A second male/female device 88', with a top section similar to that as shown in FIG. 10 (but without the vial itself being shown) is used for this purpose. In operation, the member 88' is pushed downward only to the point where the tabs 84 engage the flange 82'. In this position, the vial 38 and device 2 are held securely together but are spaced apart far enough that the needle 58 does not penetrate the cap 46 of vial 38. Nor is it pushed downward to engage and open one-way valve 56. Subsequently when it is desired to join the two materials, the member 88' is pushed further down so that the tabs 84 engage the conical flange 82, which causes the needle 58 to be pushed downward to open valve 56 and to also penetrate and open the cap 46 by the downward movement of vial 38, all as illustrated in FIG. 10. As will be understood, the valve 56 can be replaced by a clamp or other means for closing the connection between the interior of the vial 38 and the device 2. The tabs 84 on member 88' can, if desired, be fitted with levers 112 which permit one to use thumb or finger pressure to spread the tabs 84 and release the member 88' when the vial 38 is empty.

In yet another embodiment, as shown in FIG. 12 through 17, the vial adapter consists essentially of male and female fittings, such as common Luer type fittings or locking Luers. One of the fittings is connected to the vial connector and one is connected to the delivery device. Further, preferably, one of the fittings contains a check valve, or other closure means, that acts to prevent the flow of liquid from the device. It will be appreciated, that in these constructions, either the male or the female fitting can be connected to the vial connector end or vice versa.

Figure 12:
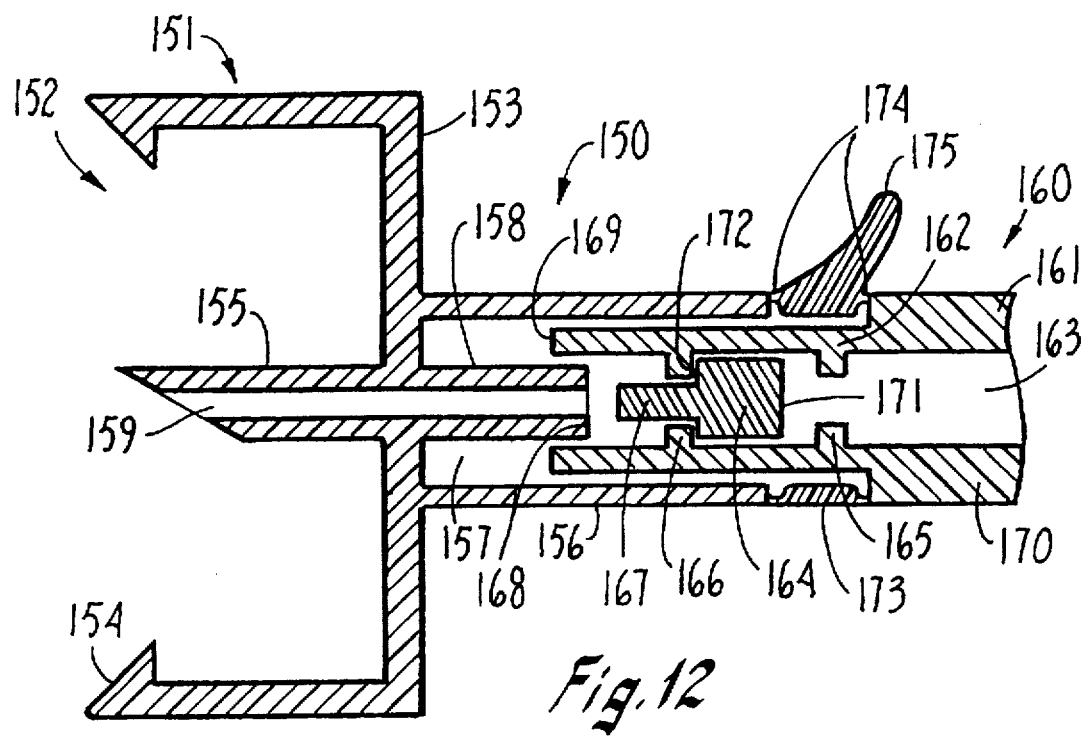
FIG. 12 is a side cross sectional view of a vial adapter in accordance with the present invention having its frangible strip in place, thereby preventing the two sections of the connector from moving relative to one another, thus maintaining the seal of the one-way valve.

Thus, referring now to FIG. 12, a drug vial adapter 150 is provided with a vial attachment end 151 that is sized and shaped to receive and lock in a drug vial (not shown). The vial attachment end 151 has an front open end 152 and a back closed end 153. As will be appreciated, drug vials typically have a rim that separates their mouth portion from their neck portion. The vial attachment end 151 of the vial adapter 150 has a vial catch 154 that is formed around the circumference of the front open end 152 of the vial attachment end 151 which acts to lock a drug vial to the vial adapter 150. In the center of the vial attachment end 151, a spike 155 is positioned. Thus, a drug vial is centered in the front open end 152 of the vial attachment end 151 and pushed longitudinally towards the back closed end 153 of the vial attachment end 151. Such action forces the spike 155 through a septum or a similar sealing means in a drug vial. A rim on a drug vial will catch on the vial catch 154, holding the vial in position with the spike 155 extending therein.

Extending distally from the back closed end 153 of the vial attachment end 151, the vial adapter 150 has a stem wall 156. The stem wall 156 defines a main channel section 157. Within the main channel section 157, a rod 158 extends. The rod 158 is in communication with the spike 155 through a first lumen 159, thus allowing fluid communication between a vial into the main channel section 157.

Distal to the vial attachment end 151 and its stem wall 156 is a connector 160. The connector 160 has a wall 161 and a recessed wall 162. The recessed wall is sized to fit within the main channel section 157 of the vial attachment end 151. Internal to the wall 161 and the recessed wall 162 of the connector 160, a second lumen 163 extends. Within the second lumen 163, there is a valve 164 that is kept in general longitudinal position with circumferential tabs 165 and 166. The valve 164, on its proximal end, has a recessed stem section 167 that extends proximally through the lumen 163 and the proximal most circumferential tab 166.

The distal end 168 of the rod 158 is sized to fit within the distal end 169 of the second lumen 163, thus allowing fluid communication between the first lumen 159 and the second lumen 163. However, the valve 164 acts to stop fluid flow from the proximal end 170 to the distal end 169 of the connector 160 because pressure exerted against the distal end 171 of the valve 164 forces the proximal edge 172 of the valve 164 against the proximal most circumferential tab 166.

The vial attachment end 151 of the vial adapter 150 is attached to the connector 160 through detachable wall section 173. The detachable wall section 173 acts to provide mechanical stability to the vial adapter as well as maintaining the channel section aseptic and sterile. In a preferred embodiment, the detachable wall section forms a seal between the vial attachment end 151 of the vial adapter 150 and the connector 160 of the vial adapter 150. There are other structures that would achieve similar results as the detachable wall section 173. For example, a resilient or flexible seal between the vial attachment end 151 of the vial adapter 150 and the connector 160 of the vial adapter 150 would be equivalent. Alternatively, a twist-off seal would provide the selectively frangible function which is desired. Some reduction in structural rigidity would be observed. However, such a sleeve would serve to seal the connection. Similarly, an o-ring or other similar structure could be provided on the sleeve. Such structure would provide an adequate seal, however, there would also be seen a reduced mechanical strengthening.

Alternatively, it will be understood that, instead of utilizing the detachable wall section, the device can be fitted with one or more detents on the connector and a detent release lever on the vial attachment end, along with threading. This configuration would provide similar mechanical strength properties as the detachable wall section and could be easily adapted to provide for aseptic or sterile closure. Moreover, such an arrangement can be completely removed from the connector 160, providing a similar advantage as the detachable wall section 173.

In the preferred embodiment, however, the detachable wall section 173 has means, such as frangible strips 174 and pull tab 175 that allow the removal of the detachable wall section 173 from the vial adapter 150. This is advantageous, since the entire vial attachment end 151 can be removed, if desired, from the vial adapter 150, leaving only the connector 160. This allows the connector 160 to be used for attachment to another connector, such as a connector on an IV set.

Figure 13:
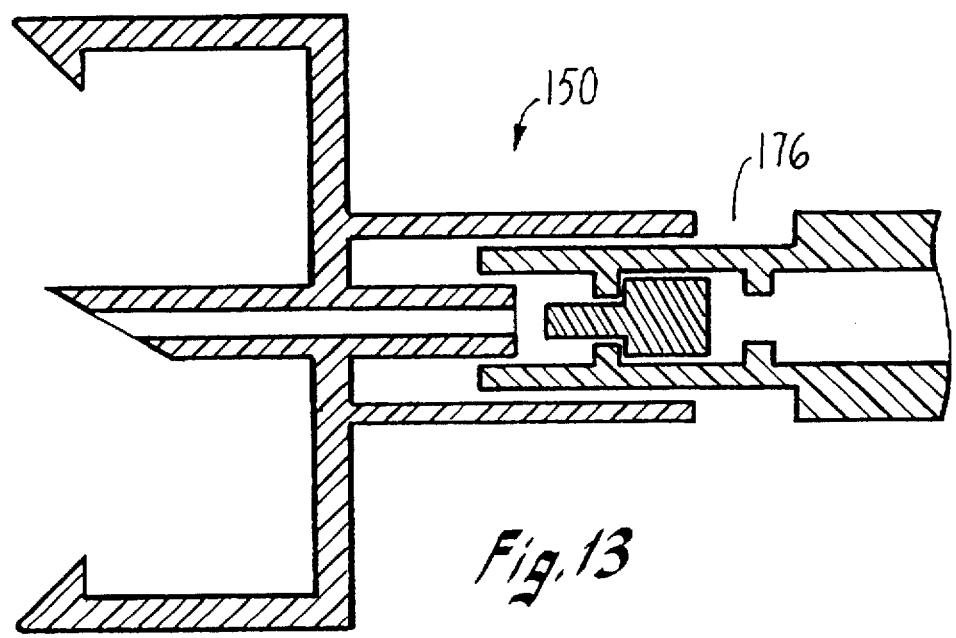
FIG. 13 is the view in FIG. 12 with the frangible strip removed.
Figure 14:
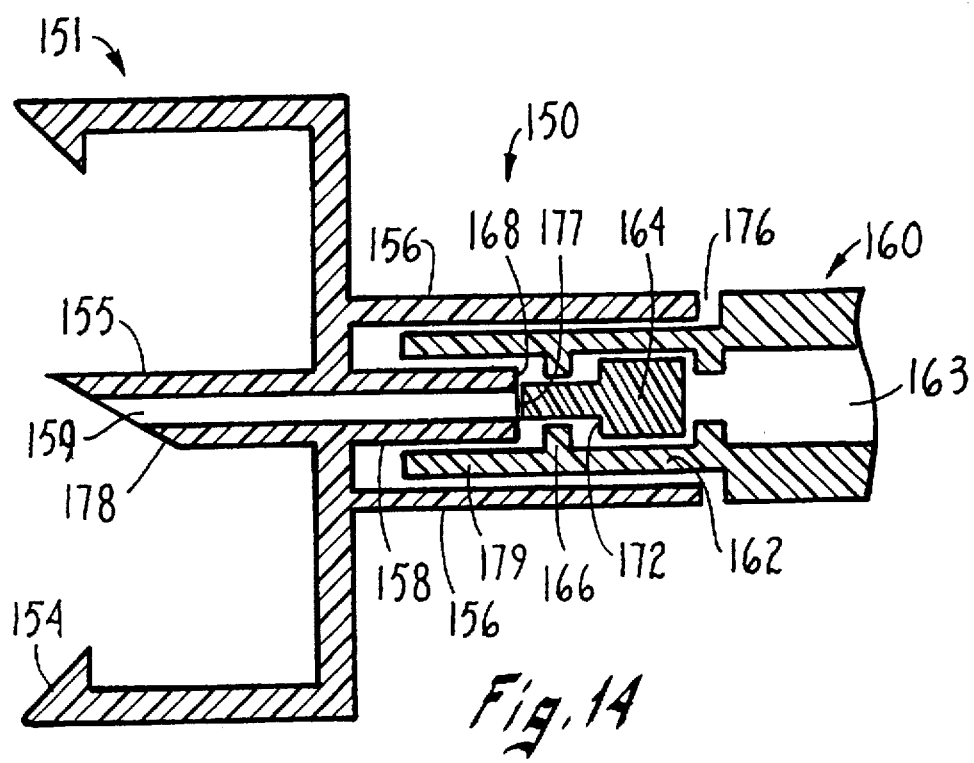
FIG. 14 is the view in FIG. 13 where the two sections of the adapter have been moved longitudinally together thereby actuating the one-way valve and allowing fluid communication through the first and second lumen.

In FIG. 13; the detachable wall section 173 has been removed leaving a void section 176 in the vial adapter 150. This void section 176, as will be seen in FIG. 14, allows the vial attachment end 151 to move distally toward the connector 160, with the stem wall 156 sliding over the recessed wall area 162 on the connector 160. This distal movement operates to move the distal end 168 of the rod 158 toward the distal end 177 of the valve 164, forcing the proximal edge 172 of the valve 164 away from the proximal most circumferential tab 166 and allowing fluid to flow from the second lumen 163 in the connector 160 into the first lumen 159 and out the distal end 178 of the spike 155.

Figure 15:
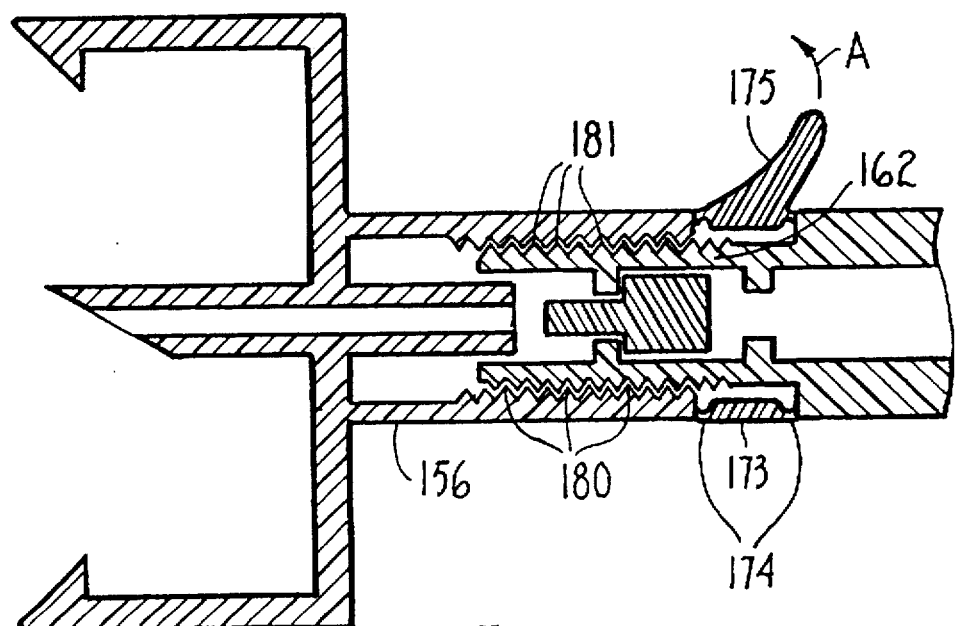
FIG. 15 is a similar view as in FIG. 12 in an embodiment where the two sections of the connector have threads.
Figure 16:
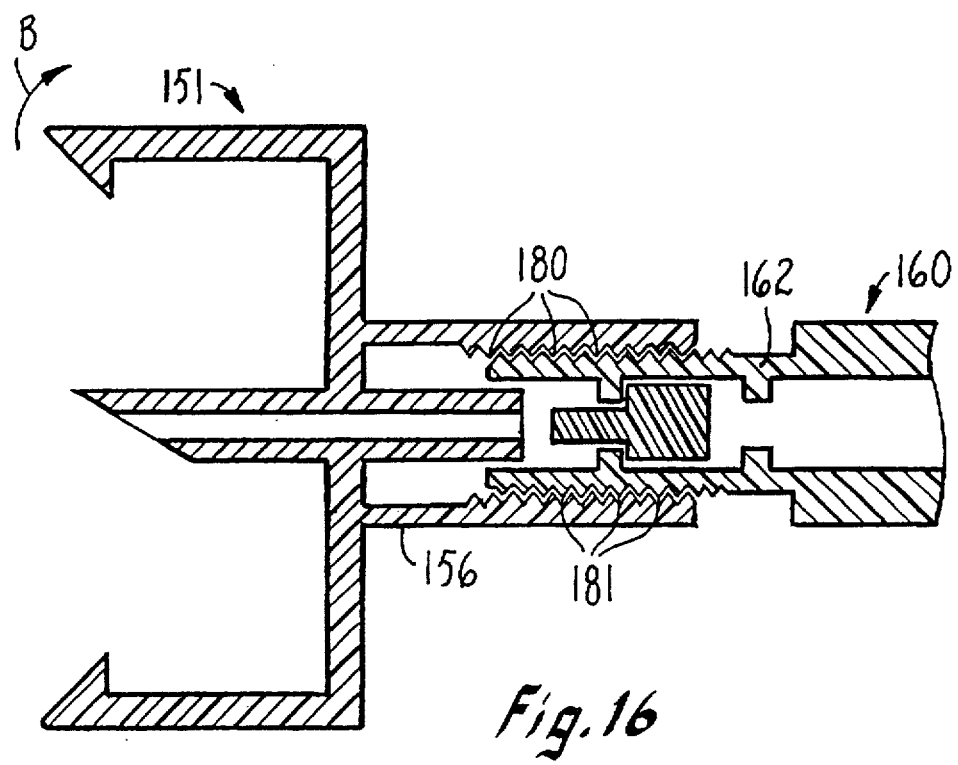
FIG. 16 is a similar view as in FIG. 13 in the embodiment shown in FIG. 15.
Figure 17:
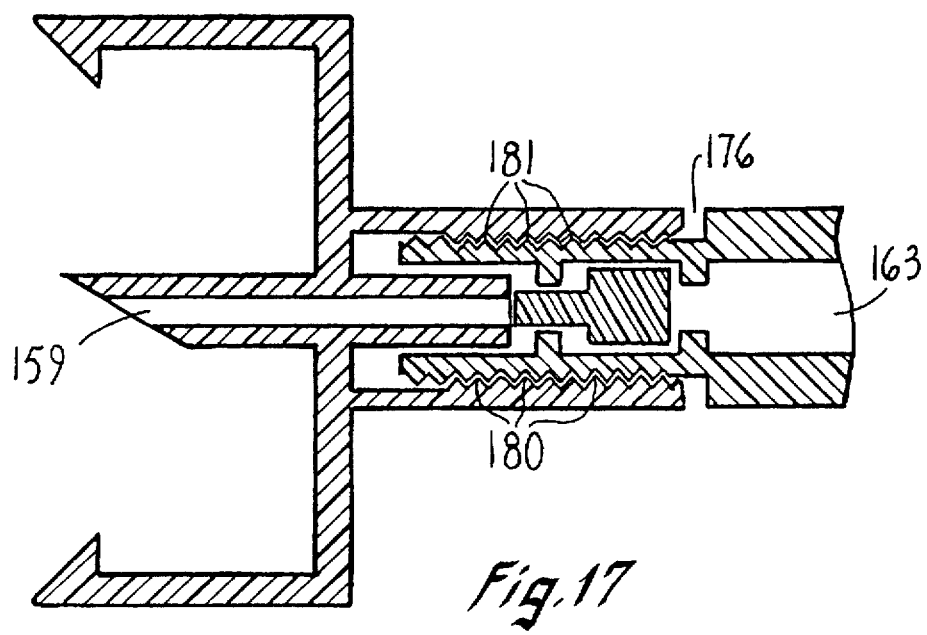
FIG. 17 is a similar view as in FIG. 14 in the embodiment shown in FIGS. 15 and 16.

As will be understood, in the above-discussed design in FIGS. 15 through 17, as easily as the vial attachment end 151 of the vial adapter 150 will slide distally toward the connector 160, it can slide proximally, falling apart. Therefore, in a preferred embodiment, the inside wall 178 of the stem wall 156 and the outside wall 179 of the recessed wall section are threaded, or are otherwise constructed so as to protect against detachment. Moreover, these designs tend to simplify the depression of the valve 164 in order to allow communication of fluid through the second and first lumens. FIGS. 15 through 17 show a model having threads 181 on the stem wall and threads 180 on the recessed wall section 162. The detachable wall section 173 is removed by pulling on pull tab 175 in the direction of arrow A. The detachable wall section will separate along frangible wall sections 174. Thereafter, in FIG. 16, the vial attachment end 151 is turned in the direction of arrow B, which turns the stem wall 156 around the recessed wall section 162 and the threads 180 and 181 will draw the stem wall 156 distally on the connector. This action, as will be seen in FIG. 17, will reduce the size of the void space 176 and also allow fluid communication between the first and second lumens 159 and 163, respectively, as discussed in more detail in connection with FIG. 14.

It will be appreciated that there are valves and closure systems that can be opened without the longitudinal motion of the vial attachment end and the connector in relation to one another. For example, there are a variety of bayonet type valve actuators. In bayonet style actuators, upon the axial twisting of one of the ends relative to the other, structure similar to the rod 158 can be caused to extend and depress the distal end of the valve. In addition, a variety of axial pressure valves are made that, when pressure is exerted external to the valve, will deform the shape of the lumen surrounding the valve closure. Alternatively, the connection between the vial adaptor and the connector can be closed by means of a clamp, valve or other closure means as described above.

It will be evident from the above that there are numerous embodiments of this invention which, while not expressly described herein, are clearly within the scope and spirit of the invention. The above description and drawings are therefore intended to be exemplary only, and the scope of the invention is to be determined solely from the appended claims.

What we claim is:

1. A method for permitting a substance in a vial to be transferred to a liquid delivery device, and contents of the delivery device to be administered to a patient, comprising, in sequence, the following steps:

reversibly attaching said vial to said delivery device;

introducing said substance into said delivery device through a connection formed and opened between said vial and said delivery device upon attachment of the vial;

reversibly closing the connection between said vial and said delivery device;

removing said vial from said delivery device; and pressurizing the contents of said delivery device for administration to said patient following the removal of said vial.

2. The method of claim 1, wherein said introducing step comprises introducing a liquid contained in said delivery device into said vial, and thereafter introducing said liquid in said vial back into said delivery device.

3. The method of claim 1, wherein said closing step is accomplished by means of a valve.

4. The method of claim 1, wherein said closing step is accomplished by means of a clamp.

5. The method of claim 1, wherein said delivery device is an I.V. bag.

6. The method of claim 1, wherein said delivery device is a pressure infusion device.

7. A method for permitting a solid substance in a vial to be transferred to a liquid delivery device containing a diluent, and contents of the device to be thereafter administered to a patient, comprising, in sequence, the following steps:

reversibly attaching said vial to said delivery device;

introducing a portion of said diluent into said vial through a connection formed and opened between said vial and said delivery device following attachment of the vial, to dissolve said solid substance;

reversibly closing the connection between said vial and said device;

removing said vial from said delivery device; and administering the contents of said device to said patient.

8. The method of claim 7, further comprising pressuring the contents of said device prior to said administering step.

9. The method of claim 7, further comprising repeating the introducing and returning steps until said solid is substantially dissolved in said diluent.

10. The method of claim 7, wherein said closing step is accomplished by means of a valve.

11. The method of claim 7, wherein said closing step is accomplished by means of a clamp.

12. The method of claim 7, wherein said device is an I.V. bag.

13. The method of claim 7, wherein said device is a pressure infusion device.

* * * * *